United States Patent
Slayton et al.

(10) Patent No.: US 11,185,719 B2
(45) Date of Patent: *Nov. 30, 2021

(54) METHODS AND SYSTEMS FOR CONTROLLING AND ACOUSTIC ENERGY DEPOSITION IN VARIOUS MEDIA

(71) Applicant: Guided Therapy Systems, LLC, Mesa, AZ (US)

(72) Inventors: Michael H. Slayton, Mesa, AZ (US); Paul Jaeger, Mesa, AZ (US)

(73) Assignee: Guided Therapy Systems LLC, Scottsdale, AZ (US)

( * ) Notice: Subject to any disclaimer, the term of this patent is extended or adjusted under 35 U.S.C. 154(b) by 527 days.

This patent is subject to a terminal disclaimer.

(21) Appl. No.: 14/600,782

(22) Filed: Jan. 20, 2015

(65) Prior Publication Data

US 2015/0202468 A1 Jul. 23, 2015

Related U.S. Application Data

(60) Provisional application No. 61/929,147, filed on Jan. 20, 2014, provisional application No. 61/991,388, filed on May 9, 2014.

(51) Int. Cl.
| | |
|---|---|
| *A61N 7/02* | (2006.01) |
| *A61N 7/00* | (2006.01) |
| *A61B 17/225* | (2006.01) |
| *A61B 17/50* | (2006.01) |
| *A61H 23/00* | (2006.01) |

(52) U.S. Cl.
CPC .............. *A61N 7/02* (2013.01); *A61B 17/225* (2013.01); *A61B 17/50* (2013.01); *A61H 23/008* (2013.01); *A61N 7/00* (2013.01); *A61N 2007/0008* (2013.01); *A61N 2007/0013* (2013.01); *A61N 2007/0017* (2013.01); *A61N 2007/0034* (2013.01); *A61N 2007/0073* (2013.01)

(58) Field of Classification Search
CPC .... A61N 7/02; A61N 7/00; A61N 2007/0008; A61N 2007/0013; A61N 2007/0017; A61N 2007/0034; A61N 2007/0073; A61B 17/225; A61B 17/50; A61H 23/008
See application file for complete search history.

(56) References Cited

U.S. PATENT DOCUMENTS

| | | | | |
|---|---|---|---|---|
| 6,488,626 B1* | 12/2002 | Lizzi | ................... | A61B 8/0858 600/437 |
| 2007/0106157 A1* | 5/2007 | Kaczkowski | .......... | A61B 5/015 600/438 |
| 2008/0009774 A1* | 1/2008 | Capelli | ..................... | A61N 7/02 601/3 |
| 2011/0251528 A1* | 10/2011 | Canney | .................... | A61N 7/02 601/3 |
| 2011/0263967 A1* | 10/2011 | Bailey | .................... | A61B 8/085 600/411 |
| 2012/0143056 A1* | 6/2012 | Slayton | .................... | A61N 7/00 600/439 |

* cited by examiner

*Primary Examiner* — Hien N Nguyen
(74) *Attorney, Agent, or Firm* — Quarles & Brady LLP (57) ABSTRACT

A system and method for controlling acoustic energy deposition in various media or objects are disclosed. The system and method can generate an acousto-mechanical or acousto-elastic effect in the various media or objects. The acousto-mechanical or acousto-elastic effect can induce a fragmentation of the media or objects.

27 Claims, 10 Drawing Sheets

METHODS AND SYSTEMS FOR CONTROLLING AND ACOUSTIC ENERGY DEPOSITION IN VARIOUS MEDIA

CROSS-REFERENCE TO RELATED APPLICATIONS

This application is based on, claims priority to, and incorporates herein by references U.S. Provisional Patent Application Ser. Nos. 61/929,147, filed Jan. 20, 2014, and 61/991,388, filed May 9, 2014.

BACKGROUND

Acoustic energy deposition currently involves continuous wave ultrasound or pulsed ultrasound with pulses on the order of tens of microseconds to seconds. Initial applications of ultrasound energy were deployed for burning materials through a thermal effect. More recently, ultrasound methods have been developed which take advantage of cavitation. However, these methods require deposition of large amounts of energy in order to be effective. Moreover, these methods produce macro-scale effects and are not capable of providing effects at the molecular level.

Optical systems have been developed to introduce opto-acoustical or opto-mechanical effects in materials. However, the opto-acoustical and opto-mechanical effects involves transformation of optical energy into acoustical energy. As is generally true with energy transformation of this sort, the conversion is very inefficient and requires much more optical energy than would be required if ultrasound energy were to be directly deployed for this purpose.

These existing methods have drawbacks; therefore new approaches for the controlled delivery of acoustic energy in various media are required.

SUMMARY

The present disclosure overcomes the aforementioned drawbacks by presenting systems and methods for controlling acoustic energy deposition in various media.

In one aspect, this disclosure provides a method of inducing an acousto-mechanical or acousto-elastic effect in a target zone of a medium. The method can include one or more of the following steps: coupling an ultrasound energy source to the target zone of the medium; and directing a pulsed first ultrasound energy from the ultrasound energy source into the target zone of the medium, thereby initiating an acousto-mechanical or acousto-elastic effect in the target zone. The ultrasound energy source can be configured to produce a pulsed first ultrasound energy having a frequency of between 100 kHz and 200 MHz and a pulse duration of between 1 picosecond and 1 millisecond. The ultrasound energy source can be configured to produce a pulsed first ultrasound energy having a frequency of between 100 kHz and 200 MHz, a pulse duration of between 1 picosecond and 1 millisecond, and a power of between 1 kW and 50 kW. The pulsed first ultrasound energy can have a pulse energy from 500 nJ to 5 J.

In another aspect, this disclosure provides a method of inducing an acousto-mechanical or acousto-elastic effect in an object embedded in a medium. The method can include one or more of the following steps: coupling an ultrasound energy source to the object; and directing a pulsed first ultrasound energy from the ultrasound energy source into the object, thereby initiating an acousto-mechanical or acousto-elastic effect in the object that exceeds a fragmentation threshold of the object. The ultrasound energy source can be configured to produce a pulsed first ultrasound energy having a frequency of between 100 kHz and 200 MHz and a pulse duration of between 1 picosecond and 1 millisecond. The ultrasound energy source can be configured to produce a pulsed first ultrasound energy having a frequency of between 100 kHz and 200 MHz, a pulse duration of between 1 picosecond and 1 millisecond, and a power of between 1 kW and 50 kW. The pulsed first ultrasound energy can have a pulse energy from 500 nJ to 5 J.

In yet another aspect, this disclosure provides an ultrasound treatment system. The ultrasound treatment system can include an ultrasound source and a control system. The ultrasound source can be configured to emit a propagating ultrasound energy having a propagating ultrasound pulse duration between 100 ps and 1 ms, a propagating ultrasound pulse power ranging from 1 kW to 50 kW, and a propagating ultrasound frequency between 100 kHz and 200 MHz. The control system can be configured to direct the ultrasound energy source to emit the propagating ultrasound energy to a target zone within a medium at an intensity gain between 500 and 25,000, thereby initiating an acousto-mechanical or acousto-elastic effect within the target zone.

In a further aspect, this disclosure provides a method of treating a target zone of a medium. The method can include one or more of the following steps: coupling an ultrasound energy source to the target zone of the medium; and initiating, using a single ultrasound energy pulse from the ultrasound energy source, an acousto-mechanical or acousto-elastic effect in the target zone that exceeds a fragmentation threshold of the medium.

In another aspect, this disclosure provides a method of treating an object embedded in a medium. The method can include one or more of the following steps: coupling an ultrasound energy source to the object embedded in the medium; and initiating, using a single ultrasound energy pulse from the ultrasound energy source, an acousto-mechanical or acousto-elastic effect in the object that exceeds a fragmentation threshold of the object.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices, and methods relating to improved ultrasound treatment efficiency and operation are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

The various embodiments may be described herein in terms of various functional components and processing steps. It should be appreciated that such components and steps may be realized by any number of hardware components configured to perform the specified functions. For example, various embodiments may employ various cosmetic enhancement devices, visual imaging and display devices, input terminals and the like, which may carry out a variety of functions under the control of one or more control systems or other control devices. In addition, the embodiments may be practiced in any number of medical, non-medical, or cosmetic contexts and that the various embodiments relating to a method and system for acoustic tissue treatment as described herein are merely indicative of some of the examples of the applications for use in medical treatment or cosmetic enhancement. For example, the principles, features and methods discussed may be applied to any medical, non-medical, or cosmetic application. Further, various aspects of the various embodiments may be suitably applied to medical, non-medical, or cosmetic applications.

As used herein, the term cosmetic enhancement can refer to procedures, which are not medically necessary and are used to improve or change the appearance of a portion of the body. Since it is not medically indicated for improving one's physical well-being, cosmetic enhancement is typically an elective procedure. As used herein, cosmetic enhancement does not diagnose, prevent, treat, or cure a disease or other medical condition. Furthermore, cosmetic enhancement is not a method for treatment of the human or animal body by surgery or therapy nor a diagnostic method practiced on the human or animal body. Cosmetic enhancement is a non-surgical and non-invasive procedure. In some aspects, cosmetic enhancement can be a non-surgical and non-invasive procedure that is performed at home by a user who is not a medical professional.

As used herein, the term "lesion" shall refer to a void, a lesion, or a combination thereof, unless the context clearly dictates otherwise.

As used herein, the term "fragmentation" shall refer to any pressure- or temperature-induced expansion within a material that breaks apart the material, including a micro-explosion, a fragmentation, or a combination thereof, unless the context clearly dictates otherwise.

This disclosure provides systems and methods for controlling acoustic energy deposition in a medium.

Figure 1:
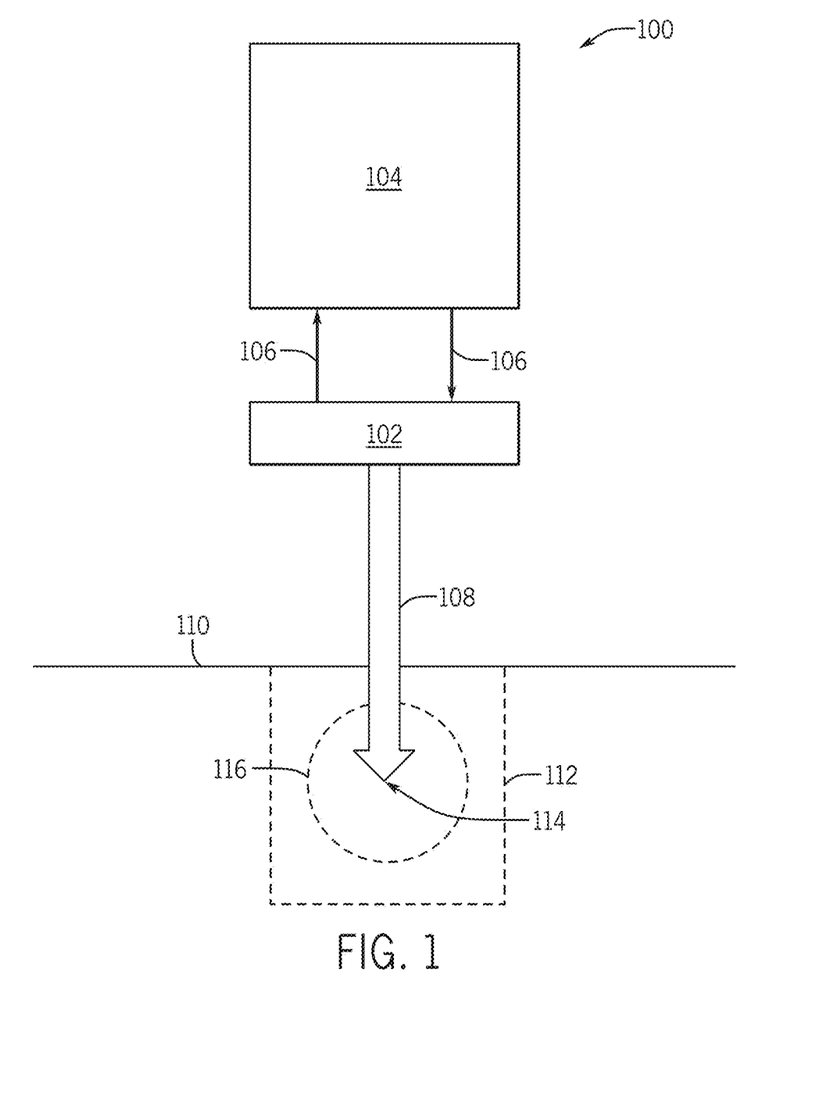
FIG. 1 is a block diagram illustrating an exemplary ultrasound delivery system, according to one aspect of the present disclosure.

Referring to FIG. 1, this disclosure provides an ultrasound delivery system 100. The ultrasound delivery system can include an ultrasound energy source 102 and a control system 104, which can be electronically coupled to one another via one or more communication conduits 106. The one or more communication conduits 106 can be wired or wireless. The ultrasound energy source 102 can be configured to emit propagating ultrasound energy 108. The control system 104 can be configured to direct the ultrasound energy source 102 to emit propagating ultrasound energy 108.

Still referring to FIG. 1, this disclosure provides systems and methods where the ultrasound energy source 102 can transmit ultrasound energy 108 across an optional boundary 110, such as a surface, and into a region of interest ("ROI") 112. The propagating ultrasound energy 108 can be delivered to a target zone 114 within the ROI 112. The propagating ultrasound energy 108 can create an acoustic energy field 116 within the ROI 112. The ROI 112 can include a medium, as described herein.

In certain aspects, the ultrasound energy source 102 can be positioned within an ultrasound probe. The ultrasound probe can optionally be handheld. The control system 104 can be located within the ultrasound probe or remote from the ultrasound probe.

Figure 2:
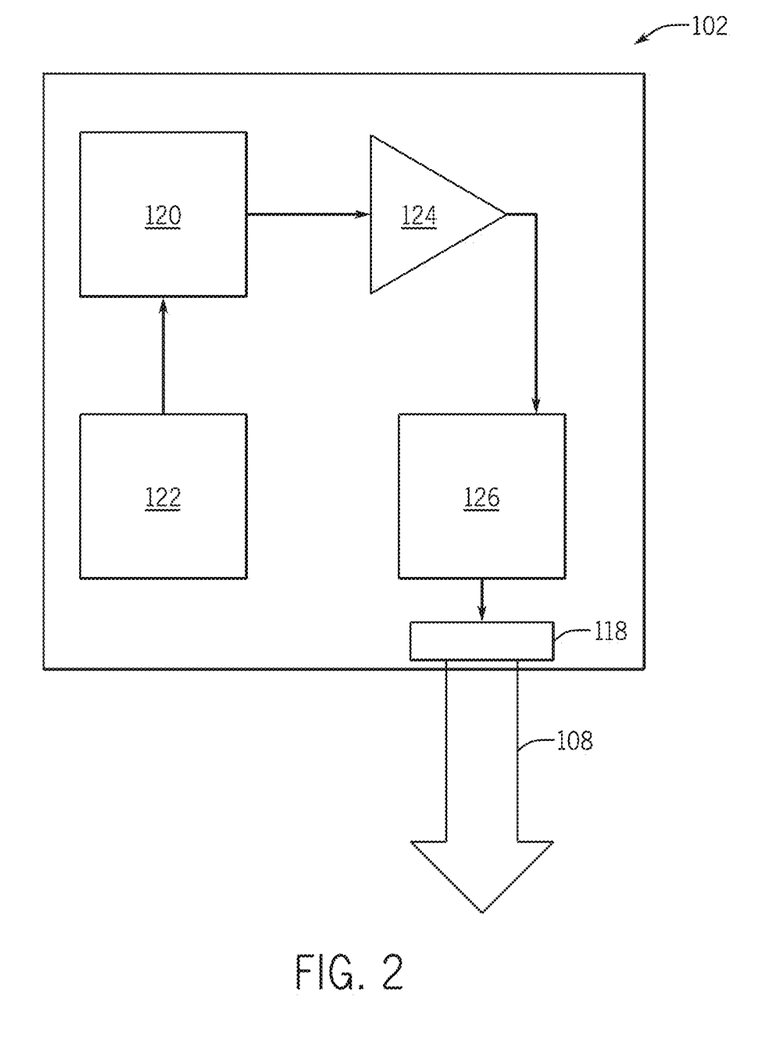
FIG. 2 is a block diagram illustrating an exemplary ultrasound energy source, according to one aspect of the present disclosure.

Referring to FIG. 2, the ultrasound energy source 102 can include a transducer 118, which is configured to emit propagating ultrasound energy 108. The ultrasound energy source can further include a function generator 120, which can be powered by a power supply 122. The function generator 120 can be a radiofrequency ("RF") generator, a frequency generator, a pulse generator, a waveform generator, or a combination thereof. The power supply 122 can be located within the ultrasound energy source 102 or remote from the ultrasound energy source 102. The function generator can provide a drive signal to the transducer 118 that initiates the emission of propagating ultrasound energy 108. The drive signal can have a drive frequency and a drive amplitude. The drive signal can be an RF signal. The ultrasound energy source 102 can optionally include an amplifier 124 that is configured to receive the drive signal, controllably amplify the drive signal to produce an amplified drive signal, and transmit the amplified drive signal to the transducer 118. The ultrasound energy source 102 can further optionally include an impedance matching network 126. The impedance matching network 126 can be configured to adjust the effective impedance or the load of the transducer 118 to match the impedance of the function generator 120 or the amplifier 124. The impedance matching network 126 can be configured to receive the drive signal from the function generator 120 and transmit a matched drive signal to the transducer 118 or to receive the amplified drive signal from the amplifier 124 and transmit a matched, amplified drive signal to the transducer 118.

In certain aspects, the propagating ultrasound energy 108 can be pulsed. The propagating ultrasound energy 108 can have a propagating ultrasound pulse duration ranging from 100 ps to 1 ms, including but not limited to, a propagating ultrasound pulse duration ranging from 100 ps to 1 µs, from 100 ps to 100 µs, from 500 ps to 500 ns, from 500 ps to 750 ns, from 1 ns to 10 µs, from 1 ns to 500 µs, from 200 ns to 1 ms, from 500 ns to 500 µs, from 1 µs to 50 µs, from 1 µs to 1 ms, or combinations of the lower and upper bounds of those ranges which are not explicitly set forth. The propagating ultrasound energy 108 can have a propagating ultrasound pulse power ranging from 1 kW to 50 kW, including but not limited to, a propagating ultrasound pulse power ranging from 1 kW to 5 kW, or from 1 kW to 10 kW. The propagating ultrasound energy 108 can have a propagating ultrasound pulse energy ranging from 500 nJ to 5 J, including but not limited to, a propagating ultrasound pulse energy ranging from 500 nJ to 2.5 mJ, from 500 nJ to 37.5 mJ, from 500 nJ to 100 mJ, from 500 nJ to 500 mJ, from 200 µJ to 5 J, from 500 µJ to 5 J, from 1 mJ to 250 mJ, from 1 mJ to 5 J, or combinations of the lower and upper bounds of those ranges which are not explicitly set forth. Ultrasound pulse durations described herein correspond to the duration of the ultrasound pulse itself and not the duration of a drive pulse or any other pulses related to the generation of ultrasound. Ultrasound pulse durations can be measured as a −6 dB pulse beam-width or a −3 dB pulse beam width.

In certain aspects, the propagating ultrasound energy 108 can have a specific frequency. The propagating ultrasound energy 108 can have a propagating ultrasound frequency ranging from 100 kHz to 200 MHz, including but not limited to, a propagating ultrasound frequency ranging from 500 kHz to 25 MHz, from 500 kHz to 200 MHz, from 1 MHz to 5 MHz, from 1 MHz to 7 MHz, from 1 MHz to 10 MHz, from 1 MHz to 20 MHz, from 1 MHz to 25 MHz, from 1 MHz to 30 MHz, from 1 MHz to 200 MHz, from 2 MHz to 5 MHz, from 2 MHz to 10 MHz, from 2 MHz to 200 MHz, or combinations of the lower and upper bounds of those ranges which are not explicitly set forth.

In certain aspects, the ultrasound energy source 102 can be configured to deliver propagating ultrasound energy 108 to the target zone 116 with an intensity gain relative to the intensity immediately after emission from the ultrasound energy source 102. The intensity gain can be in a range from 500 to 25,000, including but not limited to, a range from 1000 to 10,000. The intensity gain can be at least 500 or at least 1000.

In certain aspects, the ultrasound delivery system 100 can further include an ultrasound imaging module configured to image at least a portion of the ROI 112. The ultrasound imaging module can be located within the ultrasound probe or remote from the ultrasound probe.

In certain aspects, the ultrasound delivery system 100 can further include a secondary ultrasound energy source configured to delivery a secondary propagating ultrasound energy to the ROI 112 or the target zone 114 thereby establishing a secondary ultrasound energy field therein. A set of parameters for delivering the secondary ultrasound energy can include a secondary ultrasound frequency ranging from 100 kHz to 200 MHz, a secondary ultrasound power ranging from 1 kW to 10 kW, and a secondary ultrasound pulse duration ranging from 500 µs to 10 s. Delivering secondary ultrasound energy under these conditions can initiate a thermal effect, a cavitation effect, or a combination thereof in the target zone 114. For certain applications, the secondary ultrasound frequency can range from about 500 kHz to 25 MHz, from 500 kHz to 200 MHz, from 1 MHz to 5 MHz, from 1 MHz to 7 MHz, from 1 MHz to 10 MHz, from 1 MHz to 20 MHz, from 1 MHz to 25 MHz, from 1 MHz to 30 MHz, from 1 MHz to 200 MHz, from 2 MHz to 5 MHz, from 2 MHz to 10 MHz, from 2 MHz to 200 MHz, or combinations of the lower and upper bounds of those ranges which are not explicitly set forth. For certain applications, the secondary ultrasound power can range from 1 kW to 10 kW. For certain applications, the secondary pulse duration can range from 500 µs to 1 ms, from 500 µs to 10 ms, from 500 µs to 100 ms, from 500 µs to 1 s, from 1 ms to 50 ms, from 1 ms to 500 ms, from 1 ms to 1 s, from 1 ms to 10 s, from 50 ms to 100 ms, from 50 ms to 1 s, from 50 ms to 10 s, from 100 ms to 1 s, from 500 ms to 10 s, or from 1 s to 10 s, or combinations of the lower and upper bounds of those ranges which are not explicitly set forth.

In certain aspects, the ultrasound delivery system 100 can further include a secondary energy source configured to delivery a secondary energy to at least a portion of the ROI 112. The secondary energy source can be a photon-based energy source, an RF energy source, a microwave energy source, a plasma source, a magnetic resonance source, or a mechanical device capable of generating positive or negative pressures. Examples of a photon-based energy source include, but are not limited to, a laser, an intense pulsed light source, a light emitting diode, and the like. The secondary energy source can be located within the ultrasound probe or remote from the ultrasound probe. The secondary energy source can be configured to deliver the secondary energy before, during, or after the delivery of the propagating ultrasound energy 108. In certain aspects, the ultrasound delivery system 100 can further include an energy sink configured to remove energy from the ROI 112, for example, by providing a cooling effect the ROI 112.

Figure 3A:
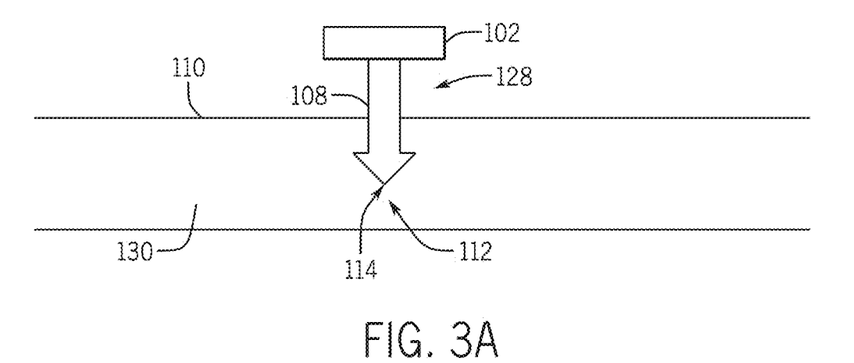
FIG. 3A is a cross-sectional view illustrating one stage of an exemplary method, according to one aspect of the present disclosure.
Figure 3B:
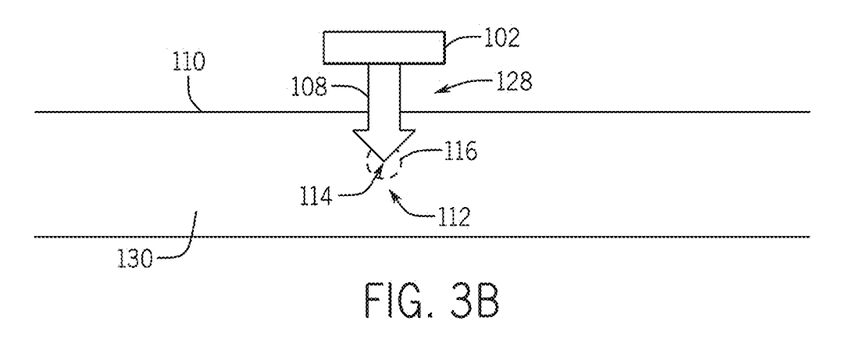
FIG. 3B is a cross-sectional view illustrating one stage of an exemplary method, according to one aspect of the present disclosure.
Figure 3C:
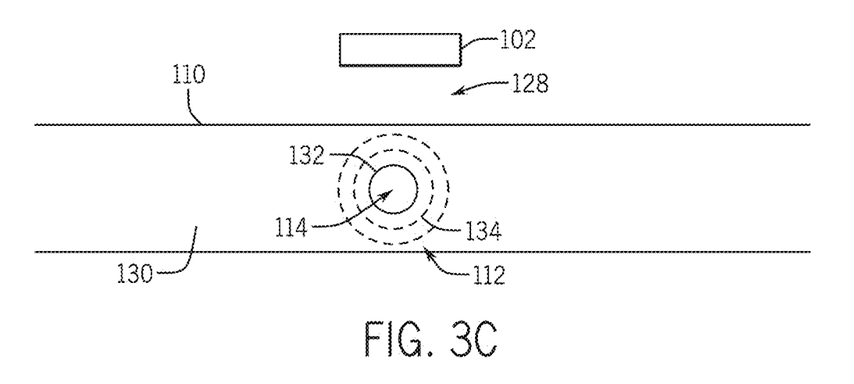
FIG. 3C is a cross-sectional view illustrating one stage of an exemplary method, according to one aspect of the present disclosure.

Referring to FIGS. 3A, 3B, and 3C, a series of cross-sectional views are shown of an ultrasound energy source 102 directing propagating ultrasound energy 108 through a first medium 128, which can be a liquid, and into a target medium 130, which can be a solid, and the resulting effect. The target medium 130 can include a ROI 112 and a target zone 114. The first medium 128 and the target medium 130 can have a boundary 110 separating them, which can be a forward surface of the target medium 130.

Referring to FIG. 3A, the cross-sectional view is shown before an acoustic energy field 116 has been established within the target medium 130. Referring to FIG. 3B, the cross-sectional view is shown as the propagating ultrasound energy 108 passes through the boundary 110 and interacts with the target medium 130 to produce an acoustic energy field 116, which can generate a non-linear effect within the target medium 130. In certain aspects, the non-linear effect can be an acousto-mechanical effect, an acousto-elastic effect, or a combination thereof in the target zone 114.

Referring to FIG. 3C, the cross-sectional view is shown after the non-linear effect has caused a fragmentation in the target zone 114, which can create a lesion 132 having essentially concentric spheres 134 or other concentric shapes, such as discs, surrounding it. The fragmentation can leave the boundary 110 undamaged and intact. In certain aspects, an acoustic impedance of the target medium 130 can be greater than an acoustic impedance of the first medium 128 and the boundary 110 can be the site of an acoustic impedance mismatch between the target medium 130 and the first medium 128.

Figure 4A:
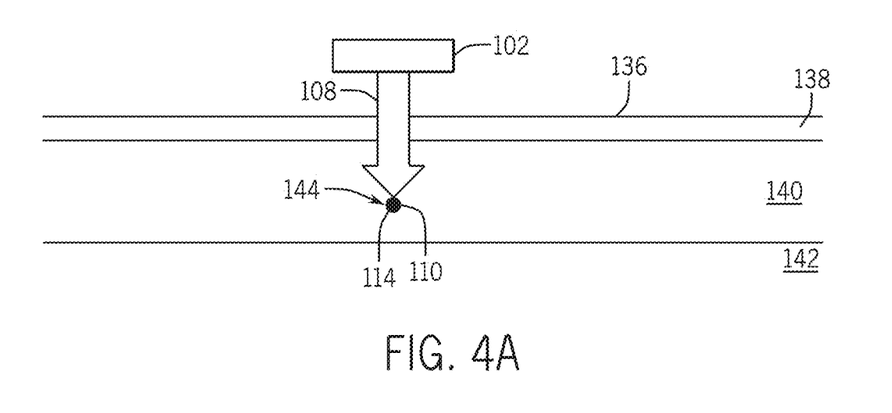
FIG. 4A is a cross-sectional view illustrating one stage of an exemplary method, according to one aspect of the present disclosure.
Figure 4B:
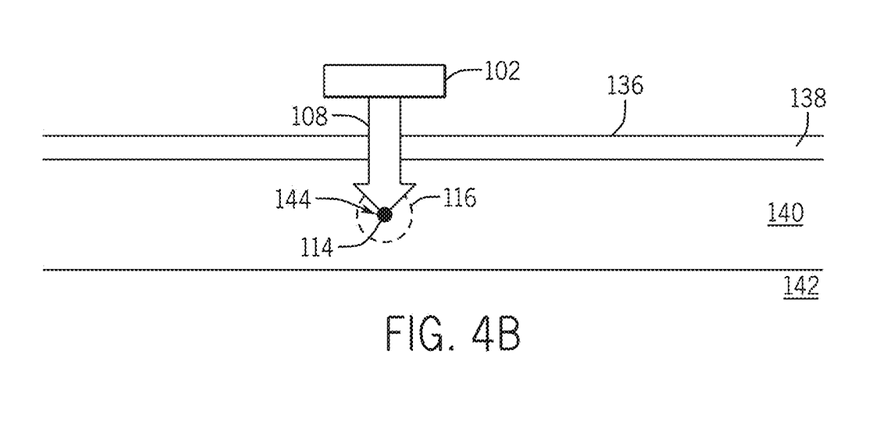
FIG. 4B is a cross-sectional view illustrating one stage of an exemplary method, according to one aspect of the present disclosure.
Figure 4C:
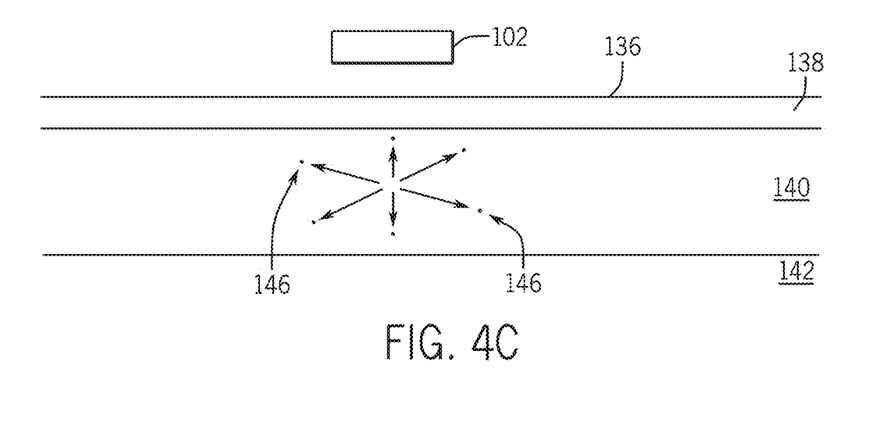
FIG. 4C is a cross-sectional view illustrating one stage of an exemplary method, according to one aspect of the present disclosure.

Referring to FIGS. 4A, 4B, and 4C, a series of cross-sectional views are shown of an ultrasound energy source 102 directing propagating ultrasound energy 108 through a first medium layer surface 136, such as a tissue surface, and a first medium layer 138, such as an epidermis layer, into a second medium layer 140, such as a dermis layer, but not into a third medium layer 142, such as a fat layer, and the resulting effect. The propagating ultrasound energy 108 can be delivered into an object 144 embedded in the second medium layer 140. The object 144 can be a target zone 114. The object 144 can consist of a solid or semi-solid material.

Referring to FIG. 4A, the cross-sectional view is shown before an acoustic energy field 116 has been established within the object 144 and surrounding portion of the second medium layer 140. A boundary 110, such as the outer surface of the object 144, can separate the object 144 from the second medium layer.

Referring to FIG. 4B, the cross-sectional view if shown as the propagating ultrasound energy 108 passes through the boundary 110 and into the object 144 to produce an acoustic energy field 116 in the object 144 and surrounding portion of the second medium layer 140, which can generate a non-linear effect within the object 144. In certain aspects, the non-linear effect can be an acousto-mechanical effect, an acousto-elastic effect, or a combination thereof in the object 144.

Referring to FIG. 4C, the cross-sectional view is shown after the non-linear effect has caused a fragmentation in the object 144, which can create a plurality of sub-particles 146. In certain aspects, the sub-particles can be absorbed by the second medium layer 140 or other surrounding media, for example, by the dermal layer and surrounding tissue using the body's immune system. In certain aspects, an acoustic impedance of the object 144 can be greater than an acoustic impedance of the second medium layer 140 and the boundary 110 can be the site of an acoustic impedance mismatch between the object 144 and the second medium layer 140.

Figure 5:
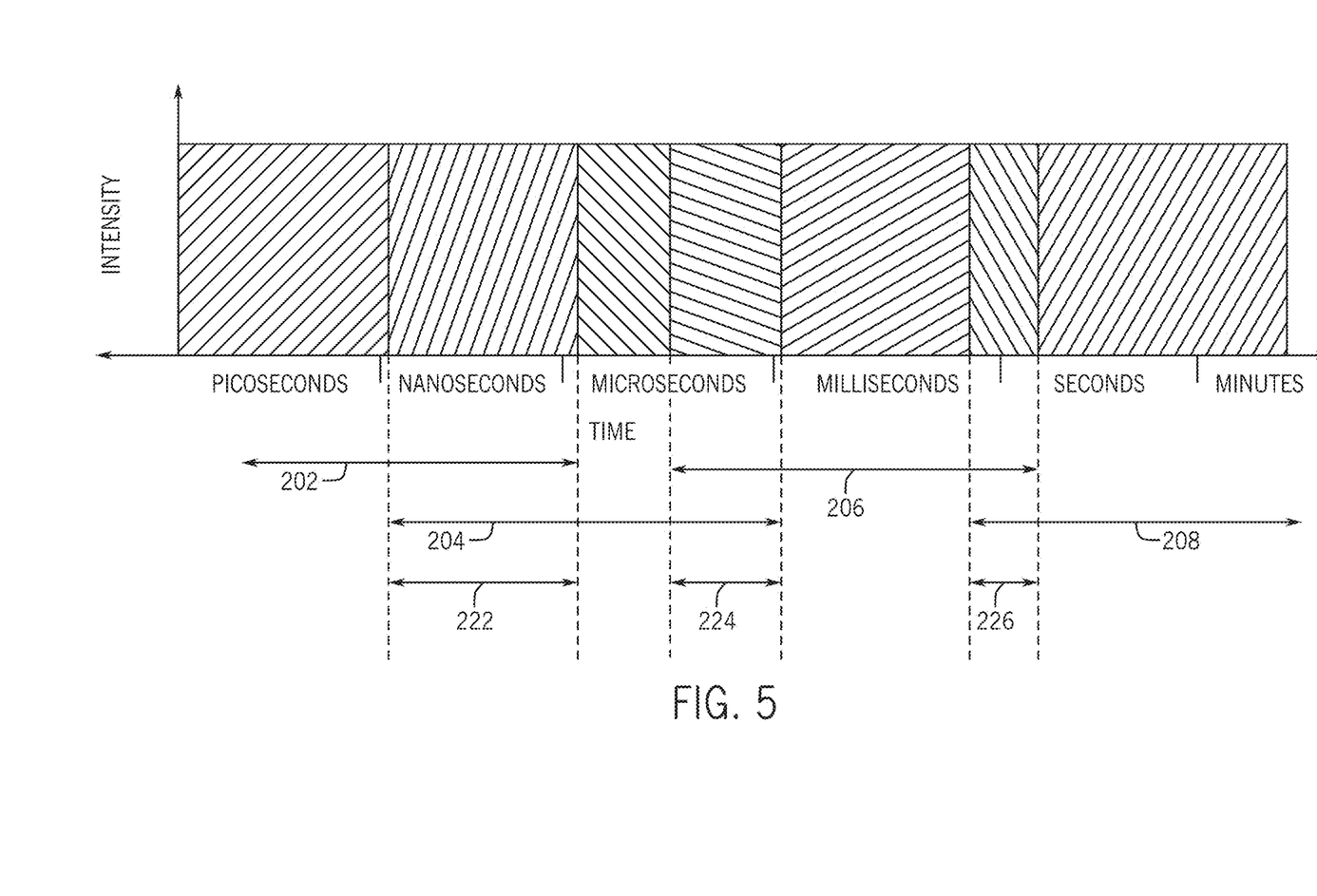
FIG. 5 is a graphical representation of the relationship between energy effects and acoustic pulse duration, according to one aspect of the present disclosure.

Referring to FIG. 5, a graphical representation 200, which has an x-axis 201 of ultrasound pulse duration represented as time and a y-axis 211 of ultrasound pulse intensity, illustrates the domains of various ultrasound sound energy initiated effects in a medium. Also as illustrated, some of the domains can overlap. These domains are approximations and the boundaries of the domain may shift for various reasons, such as changes in frequency, differences in the medium, or both. A person having ordinary skill in the art can calculate the effects of these changes using the equations described herein and equations known to those having ordinary skill in the art. These domains can be approximations in a frequency range of 1 MHz to 2 GHz. However, the frequency range can be narrower, for example, from 1 MHz to 30 MHz. In some applications, the frequency range can be from 1 MHz to 10 MHz, from 1 MHz to 7 MHz, or from 2 MHz to 5 MHz.

Still referring to FIG. 5, the first domain to be discussed is the domain of a thermal effect 208. The thermal effect raises the temperature of the medium by creating friction of molecules in the target zone of the medium from the oscillations of the acoustic energy. Different energy distribution fields can create one or more thermal effects in the medium. The energy distribution field can create a conformal elevated temperature distribution in the target zone of the medium. The ultrasound pulse duration for the domain of a thermal effect 208 is in a range from milliseconds to minutes in a frequency range, as described above.

Still referring to FIG. 5, the second domain to be discussed is the domain of cavitation 206. At sufficiently high acoustic intensities, cavitation is the formation of microbubbles in a liquid portion of a medium. The interaction of the ultrasound field with the microbubbles can cause the microbubbles to oscillate in the medium (non-inertial cavitation or dynamic cavitation) or to grow and eventually implode (inertial cavitation). During inertial cavitation, very high temperatures inside the bubbles occur, and the collapse is associated with a shock wave that can mechanically damage the medium. However, the resulting damage to the medium is typically unpredictable. The ultrasound energy is unable to cause a cavitation effect in a solid medium because a truly solid medium does not contain any liquid, which is required for formation of microbubbles. The ultrasound pulse duration for the domain of cavitation 206 is in a range from microseconds to seconds in a frequency range, as described above. There is an overlap 226 of the domain of a thermal effect 208 and the domain of cavitation 206. In the overlap 226, both of the effects, the thermal effect and the cavitation effect can occur.

Still referring to FIG. 5, the third domain to be discussed is the domain of acousto-mechanical effect 204. The acousto-mechanical effect is a destruction of a target zone in a medium by overcoming the interaction energy of the molecules in the target zone with the ultrasound energy. For example, acousto-mechanical effect can overcome a heat capacity of a medium by mechanical means, which can dramatically increase pressure in the target zone from the inside out, thus resulting in a significant increase of temperature in the target zone. The pressure, P(r,t), generated at time t and position r by the acousto-mechanical effect can be described by the following equation:

$$\nabla^2 P(r, t) - \frac{1}{v^2}\frac{\partial^2 P(r, t)}{\partial t^2} = -\frac{\beta}{C_p}\frac{\partial h(r, t)}{\partial t} \quad (1)$$

where $\beta$ is the thermal expansion coefficient of the medium, $v$ is the speed of sound in the medium, $C_p$ is the heat capacity of the medium, and $h(r,t)$ is the heat generation per unit time and volume within the medium. The acousto-mechanical effect can cause a fragmentation in the target zone of the medium. The acousto-mechanical effect can cause an increase in a pressure in the target zone above a threshold of fragmentation of the medium in the target zone. A fragmentation pressure is a minimum pressure at which a substance (for example a solid) in the target zone of a particular medium will explode (shatter, fragment). The ultrasound pulse duration for the domain of an acousto-mechanical effect 204 is in a range from nanoseconds to microseconds in a frequency range, as described above. There is an overlap 224 of the domain of cavitation 206 and the domain of an acousto-mechanical effect 204. In the overlap 224, both the cavitation and the acousto-mechanical effect can occur.

Still referring to FIG. 5, the fourth domain to be discussed is the domain of acousto-elastic effect 202. The acousto-elastic effect is an effect in a medium that arises from the combination of the pressure oscillations of an acoustic wave with the accompanying adiabatic temperature oscillations in the medium produced by the acoustic wave. Temperature of the surrounding medium is unchanged. The acousto-elastic effect is an effect in that can overcome threshold of elasticity of the molecules in the target zone of the medium. The acousto-elastic effect increases the temperature from the inside out by thermal diffusion, which can dramatically increase temperature in a target zone thus resulting in a raise in pressure in the target zone. The temperature, $T(r,t)$, generated at time t and position r by the acousto-elastic effect can be described by the following equation:

$$\frac{\partial h(r, t)}{\partial t} - \alpha \nabla^2 T(r, t) = \frac{h(r, t)}{\rho C_p} \quad (2)$$

where $\alpha$ is the thermal diffusion coefficient of the medium and $\rho$ is the density of the medium. The acousto-elastic effect can break the thermal elastic connection of the molecules in the target zone 114, which can cause a fragmentation in the target zone of the medium. The acousto-elastic effect can raise a temperature in the target zone above a fragmentation temperature of the medium in the target zone. A fragmentation temperature is a minimum temperature at which a substance (for example a solid) in the target zone of a particular medium will explode (shatter, fragment). The ultrasound pulse duration for the domain of an acousto-elastic effect 202 is in a range from picoseconds to microseconds in a frequency range, as described above. There is an overlap 222 of the domain of an acousto-mechanical effect 204 and the domain of acousto-elastic effect 202. In the overlap 222, both of the effects, the acousto-mechanical effect and the acousto-elastic effect, can occur The acousto-mechanical effect causes a massive and rapid increase in pressure in a target zone of the medium. The acousto-elastic effect causes a massive and rapid increase of temperature in a target zone of the medium. The acousto-mechanical effect and the acousto-elastic effect are different than a photo-acoustic effect. A photo-acoustic effect is the conversion of light energy into acoustic energy. The acousto-mechanical effect and the acousto-elastic effect are different than a photo-mechanical effect. A photo-mechanical effect is the conversion of light energy into mechanical energy. Accordingly, an ultrasound source cannot initiate a photo-acoustic or photo-mechanical effect. In certain aspects, an acousto-mechanical or acousto-elastic effect can initiate a change in a state of matter of a material.

Spatial control of the acoustic energy field 116 can be achieved by spatial control of the propagating ultrasound energy 108 emission. One means of achieving spatial control of the propagating ultrasound energy 108 emission is through the configuration of the ultrasound energy source 102 by way of the control system 104. For example, spatial control can be achieved through one or more of the following: varying the placement of the acoustic energy source 102; varying the orientation of the acoustic energy source 102 in any of six degrees of freedom, including three translational degrees of freedom and three rotational degrees of freedom; varying environmental parameters, such as the temperature of an acoustic coupling interface; varying the coupling agent; varying the geometric configuration of the acoustic energy source 102; varying the number of transduction elements or electrodes in the ultrasound energy source 102; utilizing one or more lenses, variable focusing devices, stand-offs, transducer backing, or acoustic matching layers; and other spatial control processes known to one having ordinary skill in the ultrasound arts. Spatial control can be facilitated by open-loop or closed-loop feedback algorithms, for example, by monitoring a signal or effect and the spatial characteristics that produce the signal or effect in order to optimize the signal or effect. The propagating acoustic energy 108 can be focused to a minimum focal spot size that is wavelength dependent.

Temporal control of the acoustic energy field 116 can be achieved by temporal control of the propagating ultrasound energy 108 emission. One means of achieving temporal control of the propagating ultrasound energy 108 emission is through the configuration of the ultrasound energy source 102 by way of the control system 104. For example, temporal control can be achieved through one or more of the following: varying a drive amplitude; varying a drive frequency; varying a drive waveform; varying drive timing sequences; varying a pulse repetition rate; apodization of the propagating ultrasound energy 108 emission; other temporal control processes known to one having ordinary skill in the ultrasound arts. Temporal control can be facilitated by open-loop or closed-loop feedback algorithms, for example, by monitoring a signal or effect and the temporal characteristics that produce the signal or effect in order to optimize the signal or effect.

Using the equations and phenomena disclosed herein and other equations and phenomena known to a person having ordinary skill in the art of ultrasound treatment, a user can determine appropriate spatial and temporal parameters to provide to the control system 104, which can direct the ultrasound energy source 102 to generate a predictable propagating ultrasound energy 108 that causes a predictable acoustic energy field 116 within a material, such as a target medium 130 or an object 144. The acoustic energy field 116 can be described by an acoustic energy function that can be mathematically determined by a person having ordinary skill in the art by using the equations and phenomena disclosed herein and other equations and phenomena known to a person having ordinary skill in the art of ultrasound treatment. The acoustic energy function can include three spatial dimensions and a time dimension.

The acoustic energy field 116 can result from an algebraic, geometric, convolved, or other mathematical combination of two or more acoustic energy fields 116 generated by one or more acoustic energy sources 102. The acoustic energy field 116 can correspond to a designed three-dimensional thermal energy distribution.

For certain applications, a set of parameters for delivering ultrasound energy can include an ultrasound frequency ranging from about 500 kHz to about 25 MHz, an ultrasound power ranging from about 1 kW to about 10 kW, an ultrasound pulse width ranging from about 500 ns to about 500 µs, and an ultrasound energy ranging from about 500 µJ to about 5 J. For certain applications, the ultrasound frequency can range from about 1 MHz to about 5 MHz. Delivering ultrasound energy under these conditions can initiate a non-linear effect in the target zone 114, such as creating a voxel of destruction in the target zone 114, initiating an acousto-mechanical effect in the target zone 114, initiating an acousto-elastic effect in the target zone 114, or a combination thereof.

For certain applications, a set of parameters for delivery ultrasound energy can include an ultrasound frequency ranging from about 1 MHz to about 10 MHz, an ultrasound power ranging from about 1 kW to about 5 kW, an ultrasound pulse width ranging from about 1 µs to about 50 µs, and an ultrasound energy ranging from about 1 mJ to about 250 mJ. Delivering ultrasound energy under these conditions can initiate a non-linear effect in the target zone 114, such as initiating an acousto-mechanical effect in the target zone. In some aspects, Delivering ultrasound energy under these conditions can initiate a non-linear effect and a mechanical effect in the target zone 114, such as initiating an acousto-mechanical effect and a cavitation effect in the target zone 114.

For certain applications, a set of parameters for delivering ultrasound energy can include an ultrasound frequency ranging from about 2 MHz to about 200 MHz, an ultrasound power ranging from about 1 kW to about 5 kW, an ultrasound pulse width ranging from about 500 ps to about 500 ns, and an ultrasound energy ranging from about 500 nJ to about 2.5 mJ. For certain applications, the ultrasound frequency can range from about 2 MHz to about 5 MHz. Delivering ultrasound energy under these conditions can initiate a non-linear effect in the target zone 114, such as initiating an acousto-mechanical effect in the target zone 114, initiating an acousto-elastic effect in the target zone 114, or a combination thereof.

For certain applications, a set of parameters for delivering ultrasound energy can include an ultrasound frequency ranging from about 100 kHz to about 200 MHz, an ultrasound power ranging from about 1 kW to about 50 kW, an ultrasound pulse width ranging from about 500 ps to about 750 ns, and an ultrasound pulse width ranging from about 500 nJ to about 37.5 mJ. Delivering ultrasound energy under these conditions can initiate a non-linear effect in the target zone 114, such as initiating an acousto-mechanical effect in the target zone 114, initiating an acousto-elastic effect in the target zone 114, or a combination thereof.

For certain applications, a set of parameters for delivering ultrasound energy can include an ultrasound frequency ranging from about 2 MHz to about 10 MHz, an ultrasound power ranging from about 1 kW to about 5 kW, an ultrasound pulse width ranging from about 200 ns to about 1 ms, and an ultrasound energy ranging from about 200 µJ to about 5 J. Delivering ultrasound energy under these conditions can initiate a non-linear effect, such as an acousto-mechanical effect, in the target zone 114. Delivering ultrasound energy under these conditions can initiate a non-linear effect in the target zone 114, such as creating a voxel of destruction in the target zone 114, initiating an acousto-mechanical effect in the target zone 114, initiating an acousto-elastic effect in the target zone 114, or a combination thereof.

In certain aspects, any of the aforementioned sets of parameters can include a range disclosed elsewhere in this disclosure that fits within the range disclosed in the set of parameters. Depending on the desired effect, interleaving pulses can be utilized to alter the temporal parameters or 2 or more pulsed ultrasound energies can be utilized to alter the spatial parameters, the temporal parameters, or both.

In certain aspects, the acousto-mechanical effect or the acousto-elastic effect generated within a medium as described herein can be sufficient to overcome Young's Modulus of the medium. Overcoming Young's Modulus can cause the medium to fragment, shatter, explode, or any combination thereof. Young's Modulus (E) can be calculated by the following equation:

$$E = \frac{\sigma}{\varepsilon} = \frac{FL_0}{A_0 \Delta L} \quad (3)$$

where $\sigma$ is the tensile stress on an object, $\varepsilon$ is the extensional strain on an object, F is the force exerted on an object, $A_0$ is the original cross-sectional area through which the force is applied, $L_0$ is the original length of the object, and $\Delta L$ is the amount by which the length of the object changes.

The ultrasound energy source 102 can be acoustically coupled, directly or indirectly, to the target zone 114, the ROI 112, the boundary 110, or any combination thereof by way of a coupling agent. In certain aspects, the acoustic coupling agent can be selected from the group consisting of water, acoustic coupling gel, other materials providing a desired transformation of acoustic impedance from the source to the target, and combinations thereof.

Figure 6A:
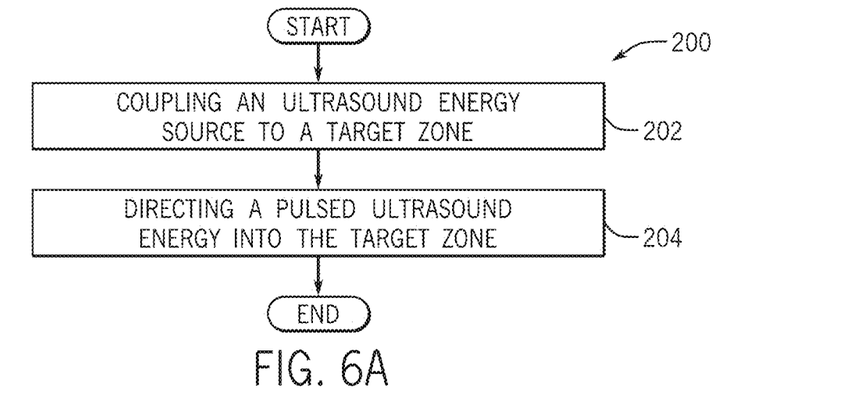
FIG. 6A is flowchart of an exemplary method, according to one aspect of the present disclosure.

Referring to FIG. 6, a method 200 of creating an acousto-mechanical or acousto-elastic effect in a target zone 114 of a target medium 130 is disclosed. At process block 202, the method 200 can include coupling an ultrasound energy source 102 to the target zone 114. At process block 204, the method 200 can include directing a pulsed ultrasound energy 108 from the ultrasound energy source 102 into the target zone 114. Directing the pulsed ultrasound energy 108 into the target zone 114 can initiate an acousto-mechanical or acousto-elastic effect in the target zone 114. The pulsed ultrasound energy 108 can have ultrasound properties as disclosed herein.

The acousto-mechanical or acousto-elastic effect generated by the method 200 can overcome a fragmentation threshold, thereby causing a fragmentation within the portion of the target medium 130 located within the target zone 114. The method 200 can further include delivering a secondary energy into the target zone 114 or the target medium 130. In some aspects, the pulsed ultrasound energy 108 can be delivered simultaneously with the secondary energy. In some aspects, the secondary energy can be delivered subsequent to the pulsed ultrasound energy 108.

The method 200 can include delivering a first energy, a second energy, a third energy, or an nth energy, simultaneously or with various time delays. The first, second, third, or nth energy can be an ultrasound energy or a secondary energy.

The method 200 can include delivering a second ultrasound energy into the target medium 130 subsequent to the delivery of the pulsed ultrasound energy 108, thereby initiating a thermal effect or a cavitational effect. In some aspects, the second ultrasound energy can have a pulse duration of greater than 100 µs.

The method 200 can include delivering a second ultrasound energy into the target zone 114 prior to the delivery of the pulsed ultrasound energy. This second ultrasound energy can create an acoustic mismatch between the target zone 114 and the rest of the target medium 130.

Figure 6B:
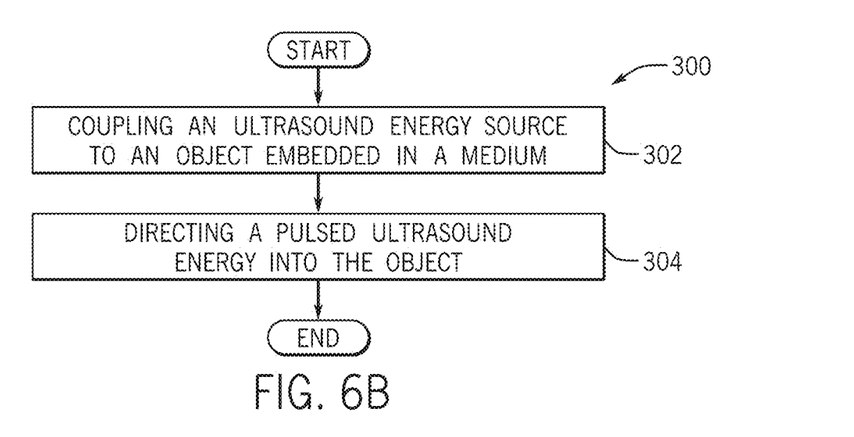
FIG. 6B is flowchart of an exemplary method, according to one aspect of the present disclosure.

Referring to FIG. 7, a method 300 of creating an acousto-mechanical or acousto-elastic effect in an object 144 embedded in a target medium 130 is disclosed. At process block 302, the method 300 can include coupling an ultrasound energy source 102 to the object 144. At process block 304, the method 300 can include directing a pulsed ultrasound energy 108 from the ultrasound energy source 102 into the object 144. Directing the pulsed ultrasound energy 108 into the object 144 can initiate an acousto-mechanical or acousto-elastic effect in the object 144. The pulsed ultrasound energy 108 can have ultrasound properties as disclosed herein. The acousto-mechanical or acousto-elastic effect generated by the method 300 can overcome a fragmentation threshold, thereby causing a fragmentation within the object 144. In certain aspects, the fragmentation can generate sub-particles.

The method 300 can further include delivering a secondary energy into the object 144 or the target medium 130. In some aspects, the pulsed ultrasound energy 108 can be delivered simultaneously with the secondary energy. In some aspects, the secondary energy can be delivered subsequent to the pulsed ultrasound energy 108.

The method 300 can include delivering a first energy, a second energy, a third energy, or an nth energy, simultaneously or with various time delays. The first, second, third, or nth energy can be an ultrasound energy or a secondary energy. The method 300 can include targeting the object 144.

The method 300 can include delivering a second ultrasound energy to the medium to generate a cavitational effect, thereby dispersing the sub-particles. The method 300 can include delivering a third ultrasound energy to the medium to create a thermal effect in the skin. The method 300 can include delivering a fourth ultrasound energy to the medium.

It should be appreciated that the method 300 is "color blind" to the color of the object, because the ultrasound energy is not absorbed in a resonant process, such as light absorption.

The methods 200 and 300 can include steps or features from one another, unless clearly dictated otherwise by context.

A medium, such as the first medium 128, the target medium 130, or the medium layers 138, 140, 142, can be any solid, liquid, gas, or combination thereof. In some aspects, a medium, such as the first medium 128, the target medium 130, or the medium layers 138, 140, 142, can be an acoustically homogeneous medium. In some aspects, a medium, such as the first medium 128, the target medium 130 or medium layers 138, 140, 142, can be an acoustically heterogeneous medium.

A medium, such as the first medium 128, the target medium 130, or the medium layers 138, 140, 142, can be selected from the group consisting of air, water, plastic, mammalian tissue, subcutaneous tissue, metal, and the like.

The object 144 can be a solid or semi-solid material. For example, the object can be selected from the group consisting of a bone fragment, a kidney stone, a gallstone, a tear-duct stone, a urinary bladder stone, a rhinolith, an enterolith, a salivary duct calculus, a tonsillith, shrapnel, a plastic particle, a sliver of wood, a metal particle, a metal oxide particle, a portion of a medical device, a pencil lead, a pigment particle, scar tissue, a calcified tissue, a sebaceous gland, a hair, a piece of cartilage, a cancerous tumor, a benign tumor, a fat cell, a muscle cell, and combinations thereof. In certain aspects, the object 144 can have an acoustic impedance that is greater than the acoustic impedance of the medium, including but not limited to, an acoustic impedance that is at least 10% greater or at least one order of magnitude greater.

When the object 144 is a calcified tissue, the method 300 can be a method for treating hyperpigmentation. In the areas of skin having hyperpigmentation, calcified tissue can be destroyed by fragmentation. The method for treating hyperpigmentation can be combined with hydroquinone treatment or application of other bleaching agents to further treat the hyperpigmentation.

In some aspects, the medium can include a sub-section of the medium having composed of the same material as the medium, but having different acoustic properties. For example, a medium can have a sub-section of the medium having a higher temperature, and therefore a different acoustic impedance, than the rest of the medium.

The systems and methods disclosed herein can be useful for medical and non-medical applications. In one aspect, the systems and methods disclosed herein can be useful for acoustic tissue treatment. In one aspect, the systems and methods disclosed herein can be useful for cosmetic applications, such as the cosmetic enhancement of skin, subcutaneous tissue layers, or a combination thereof.

EXAMPLES

Example 1

Directing Ultrasound Through Water and into Plastic to Generate an Acousto-Mechanical Effect in the Plastic Three hard plastic targets having an acoustic impedance of 2.2 mega-rayls were submerged in water having an acoustic impedance of 1.5 mega-rayls and an acoustic energy source was placed 1.5 cm from the surface of each plastic target. The ultrasound was focused to a depth of about 8.5 mm from the surface of the plastic target.

Figure 7A:
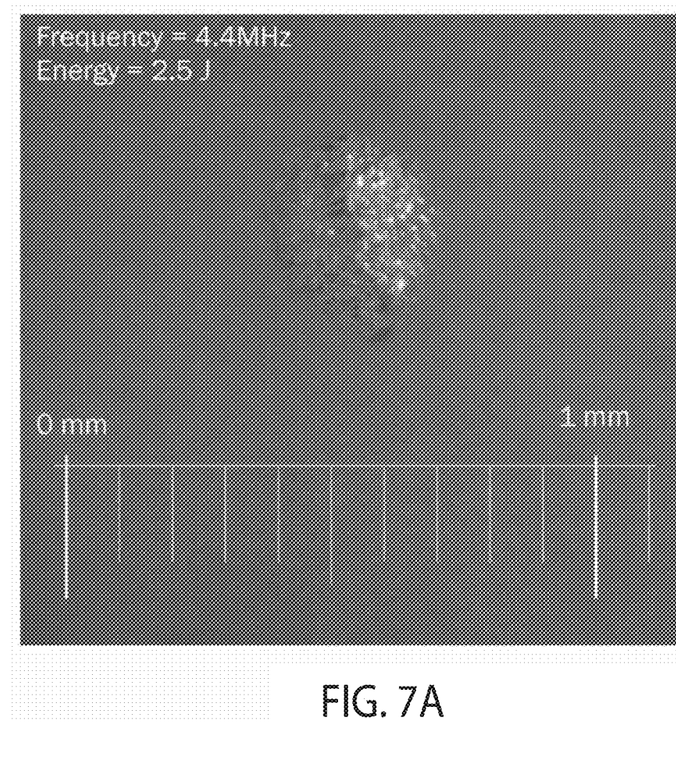
FIG. 7A is an image of a lesion generated by a thermal effect in Example 1, according to one aspect of the present disclosure.

In a first procedure using this setup, the results of which are shown in FIG. 7A, 2.5 J of ultrasound energy at a frequency of 4.4 MHz and a pulse duration of about 50 ms was directed to a focal point providing an intensity gain of about 1600. A lesion was created by a thermal effect, which resulted in the melting or vaporizing of the plastic target. As shown in FIG. 7A, the lesion contains bubbles and is melted, further confirming the thermal effect. The diameter of the lesion was approximately 300 μm in one direction and less than 400 μm in an orthogonal direction.

Figure 7B:
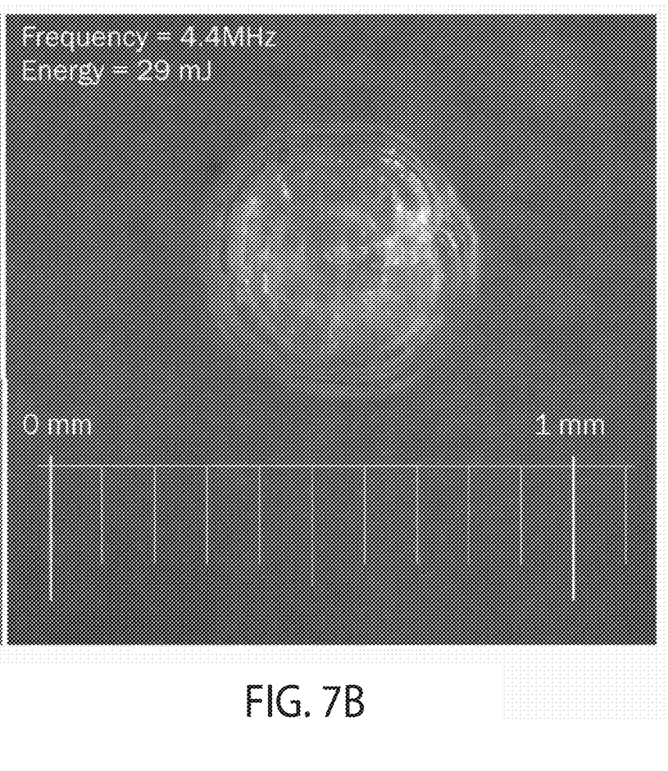
FIG. 7B is an image of a lesion generated by an acousto-mechanical effect in Example 1, according to one aspect of the present disclosure.

In a second procedure using this setup, the results of which are shown in FIG. 7B, a single pulse of ultrasound energy having a power of 1.3 kW, a pulse duration of 22 μs, an energy of 29 mJ, and a frequency of 4.4 MHz was directed to a focal point providing an intensity gain of about 1600. A lesion was created by an acousto-mechanical effect, which created a fragmentation in the plastic target. As shown in FIG. 7B, a series of concentric spheres are centered on a point at the center of the fragmentation, which confirms the fragmentation. The diameter of the lesion was approximately 450 μm.

Figure 8:
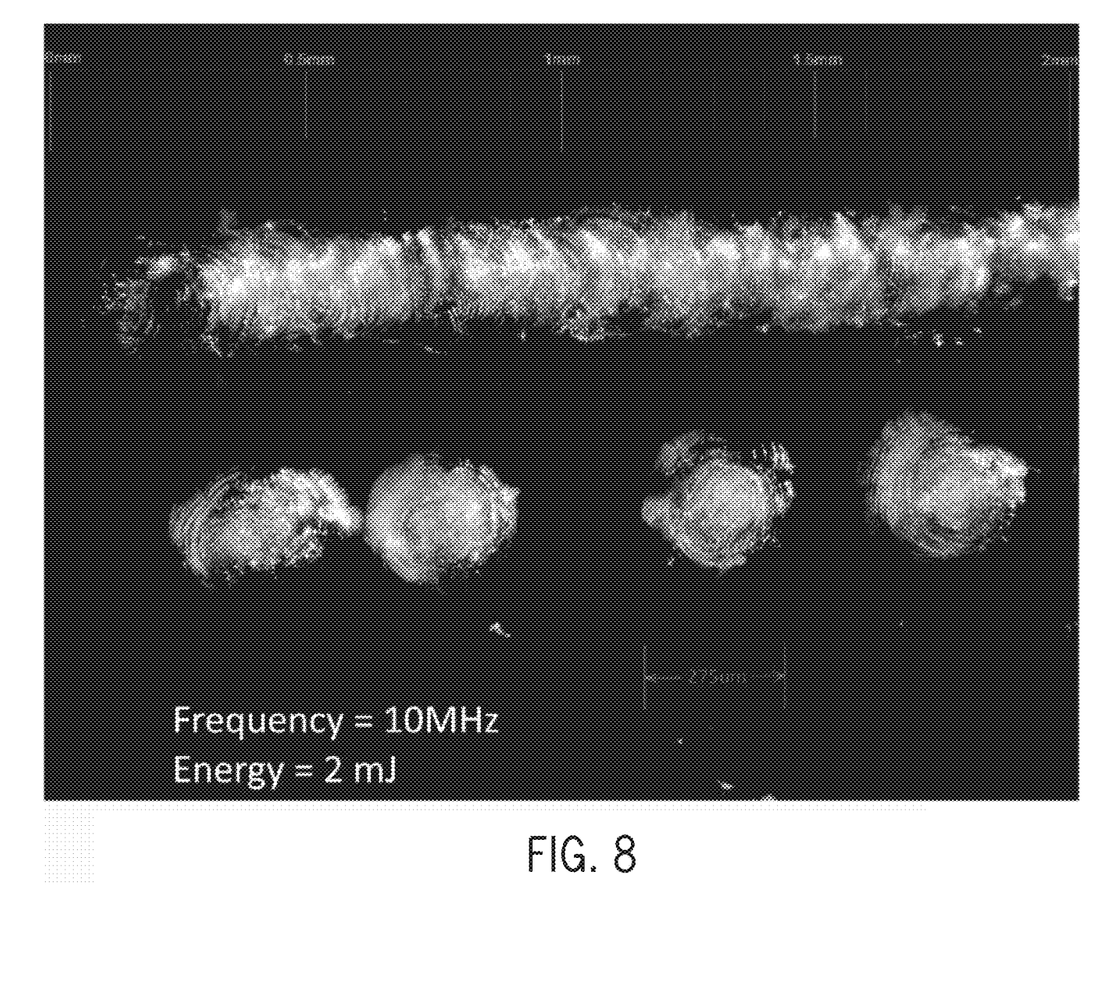
FIG. 8 is an image of a plurality of lesions generated by an acousto-mechanical effects in Example 1, according to one aspect of the present disclosure.

In a third procedure using this setup, the results of which are shown in FIG. 8, a plurality of single pulses of ultrasound energy having a power of 1.3 kW, a pulse duration of 1.5 μs, an energy of 2 mJ, and a frequency of about 10 MHz were directed to a plurality of focal points providing an intensity gain of about 1600. A plurality of lesions were created by an acousto-mechanical effect, which created a plurality of fragmentations in the plastic target. The diameter of the lesions was approximately 275 μm.

Example 2

Figure 9:
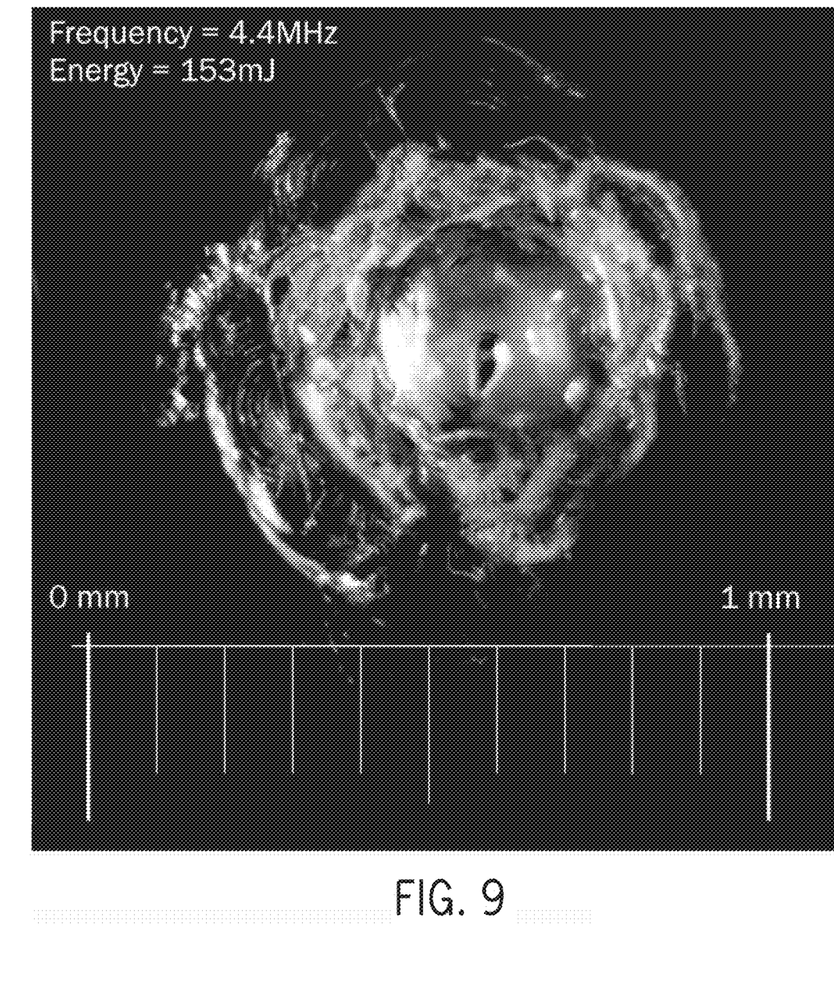
FIG. 9 is an image of a lesion generated by an acousto-mechanical effect followed by a thermal effect in Example 2, according to one aspect of the present disclosure.

Directing Ultrasound Through Water and into Plastic to Generate an Acousto-Mechanical Effect and Subsequent Thermal Effect in the Plastic The setup from Example 1 was repeated for a single plastic target. The second procedure of Example 1 was executed first, targeting a focal point. A lesion was created by an acousto-mechanical effect, as shown in FIG. 9 by the concentric spheres emanating from the fragmentation site. Then, the first procedure of Example 1 was executed, targeting the same focal point. A thermal effect was observed within the lesion created by the acousto-mechanical effect, as shown in FIG. 9 by the melting in the center of the lesion.

Example 3

Focal Depth Study of Acousto-Mechanical Effect in Plastic

Figure 10A:
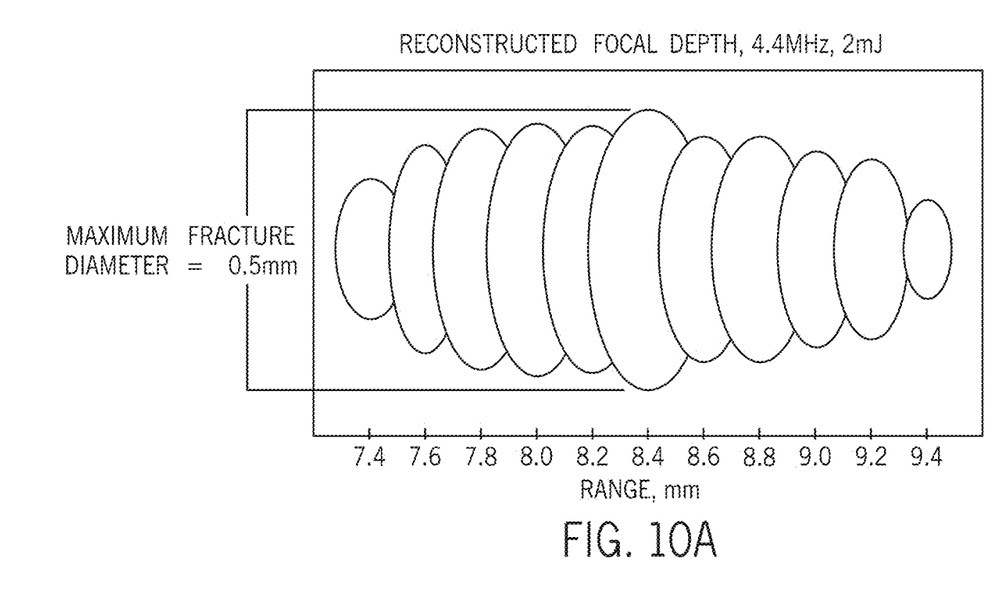
FIG. 10A is a plot of a focal depth study in Example 3, according to one aspect of the present disclosure.
Figure 10B:
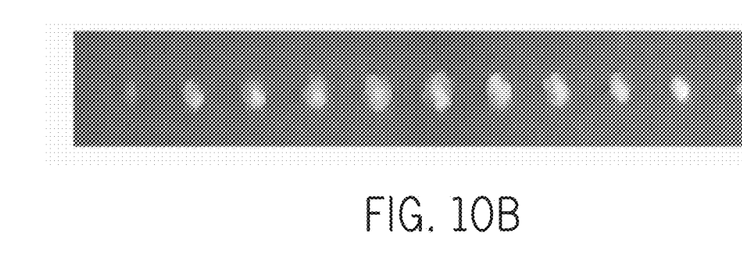
FIG. 10B is an image of a focal depth study in Example 3, according to one aspect of the present disclosure.

The setup from Example 1 was repeated for a single plastic target. The third procedure of Example 1 was executed at a plurality of different focal depths within the plastic target. A plurality of lesions were created at the plurality of different focal depths by an acousto-mechanical effect, as shown in FIG. 10B by the concentric spheres emanating from the fragmentation sites. FIG. 10A is a plot showing the relative diameter of lesions at varying focal depths, which are represented by the x-axis of the plot. The diameter of the lesion varied based on depth.

The present invention has been described above with reference to various exemplary configurations. However, those skilled in the art will recognize that changes and modifications may be made to the exemplary configurations without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound treatment as described above is suitable for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitable placement for the transducer. Moreover, while the various exemplary embodiments may comprise non-invasive configurations, system can also be configured for at least some level of invasive treatment application. These and other changes or modifications are intended to be included within the scope of the present invention, as set forth in the following claims.

The invention claimed is:

1. A method of inducing an acousto-mechanical effect in a target zone of a medium, the method comprising:
    a) coupling an ultrasound energy source to the target zone of the medium, the ultrasound energy source configured to produce a pulsed first ultrasound energy having a frequency of between 100 kHz and 200 MHz and a pulse duration of between 1 nanosecond and 1 millisecond;
    b) initiating an acousto-mechanical effect in the target zone by directing from 500 nJ to 5 J of the pulsed first ultrasound energy from the ultrasound energy source into the target zone of the medium.

2. The method of claim 1, wherein the pulse duration is between 1 nanosecond and 10 microseconds.

3. The method of claim 1, wherein the ultrasound frequency is between 1 MHz and 30 MHz.

4. The method of claim 1, the method further comprising:
    c) subsequent to step b), directing a second ultrasound energy from the ultrasound energy source or a second ultrasound energy source having an ultrasound pulse duration of at least 100 µs into the target zone, thereby initiating a second effect in the target zone.

5. The method of claim 4, wherein the second effect is a cavitational effect or a thermal effect.

6. The method of claim 4, the method further comprising repeating step b) and step c) in an alternating fashion.

7. The method of claim 1, the method further comprising:
    d) prior to step b), directing a third ultrasound energy from the ultrasound energy source or a second ultrasound energy source having an ultrasound pulse duration of at least 100 µs into the target zone, thereby initiating a third effect in the target zone.

8. The method of claim 7, wherein the third effect is altering an acoustic impedance of the target zone, thereby creating an acoustic impedance mismatch between the target zone and a portion of the medium outside the target zone.

9. The method of claim 1, wherein the acousto-mechanical effect exceeds a fragmentation threshold of the medium.

10. The method of claim 1, wherein the 500 nJ to 5 J of the pulsed first ultrasound energy directed into the target zone of the medium in step b) is a single ultrasound pulse.

11. A method of inducing an acousto-mechanical effect in an object embedded in a medium, the method comprising:
    a) coupling an ultrasound energy source to the object, the ultrasound energy source configured to produce a pulsed first ultrasound energy having a frequency of between 100 kHz and 200 MHz and a pulse duration of between 1 nanosecond and 1 millisecond;
    b) initiating an acousto-mechanical effect in the object that exceeds a fragmentation threshold of the object by directing from 500 nJ to 5 J of the pulsed first ultrasound energy from the ultrasound energy source into the object.

12. The method of claim 11, wherein the pulse duration is between 1 ns and 10 µs.

13. The method of claim 11, wherein the ultrasound frequency is between 1 MHz and 30 MHz.

14. The method of claim 11, the method further comprising:
    c) subsequent to step b), directing a second ultrasound energy from the ultrasound energy source or a second ultrasound energy source having an ultrasound pulse duration of at least 100 µs into the medium, thereby initiating a second effect in the medium.

15. The method of claim 14, wherein the second effect is a cavitational effect or a thermal effect.

16. The method of claim 11, wherein the pulsed first ultrasound energy is a single ultrasound pulse.

17. The method of claim 11, wherein the object is selected from the group consisting of a bone fragment, a kidney stone, a gallstone, a tear-duct stone, a urinary bladder stone, a rhinolith, an enterolith, a salivary duct calculus, a tonsillith, shrapnel, a plastic particle, a sliver of wood, a metal particle, a metal oxide particle, a portion of a medical device, a pencil lead, a pigment particle, scar tissue, a melanocyte, a sebaceous gland, a hair, a piece of cartilage, a cancerous tumor, a benign tumor, a fat cell, a muscle cell, and combinations thereof.

18. The method of claim 11, wherein the medium is subcutaneous tissue.

19. An ultrasound treatment system comprising:
    an ultrasound source configured to emit a propagating ultrasound energy having a propagating ultrasound pulse duration between 1 nanosecond and 1 millisecond, a propagating ultrasound pulse power ranging from 1 kW to 50 kW, and a propagating ultrasound frequency between 100 kHz and 200 MHz;
    a control system configured to initiate an acousto-mechanical effect within a target zone within a medium by directing the ultrasound energy source to emit the propagating ultrasound energy to the target zone at an intensity gain between 500 and 25,000.

20. A method of treating a target zone of a medium, the method comprising:
   a) coupling an ultrasound energy source to the target zone of the medium; and
   b) initiating, using a single ultrasound energy pulse from the ultrasound energy source, an acousto-mechanical effect in the target zone that exceeds a fragmentation threshold of the medium.

21. A method of treating an object embedded in a medium, the method comprising:
   a) coupling an ultrasound energy source to the object embedded in the medium; and
   b) initiating, using a single ultrasound energy pulse from the ultrasound energy source, an acousto-mechanical effect in the object that exceeds a fragmentation threshold of the object.

22. A method of inducing an acousto-mechanical effect in a target zone of a medium, the method comprising:
   a) coupling an ultrasound energy source to the target zone of the medium, the ultrasound energy source configured to produce a pulsed first ultrasound energy having a frequency of between 100 kHz and 200 MHz, a pulse duration of between 1 nanosecond and 1 millisecond, and a power of between 1 kW and 50 kW;
   b) initiating an acousto-mechanical effect in the target zone of the medium by directing the pulsed first ultrasound energy from the ultrasound energy source into the target zone.

23. A method of inducing an acousto-mechanical effect in an object embedded in a medium, the method comprising:
   a) coupling an ultrasound energy source to the object, the ultrasound energy source configured to produce a pulsed first ultrasound energy having a frequency of between 100 kHz and 200 MHz, a pulse duration of between 1 nanosecond and 1 millisecond, and a power of between 1 kW and 50 kW;
   b) initiating an acousto-mechanical in the object by directing the pulsed first ultrasound energy from the ultrasound energy source into the object.

24. The method of claim 1, the pulsed first ultrasound energy having a frequency of between 1 MHz and 5 MHz, a pulse duration of between 500 ns and 500 μs, and a power of between 1 kW and 10 kW.

25. The method of claim 1, the pulsed first ultrasound energy having a frequency of between 1 MHz and 10 MHz, a pulse duration of between 1 μs and 50 μs, and a power of between 1 kW and 5 kW, the initiating of step b) including directing from 1 mJ to 250 mJ of the pulsed first ultrasound energy from the ultrasound energy source into the target zone of the medium.

26. The method of claim 1, the pulsed first ultrasound energy having a frequency of between 2 MHz and 200 MHz, a pulse duration of between 1 ns and 500 ns, and a power of between 1 kW and 5 kW, the initiating of step b) including directing from 500 nJ to 2.5 mJ of the pulsed first ultrasound energy from the ultrasound energy source into the target zone of the medium.

27. The method of claim 1, the pulsed first ultrasound energy having a pulse duration of between 1 ns and 750 ns and a power of between 1 kW and 50 kW, the initiating of step b) including directing from 500 nJ to 37.5 mJ of the pulsed first ultrasound energy from the ultrasound energy source into the target zone of the medium.

\* \* \* \* \*

UNITED STATES PATENT AND TRADEMARK OFFICE
CERTIFICATE OF CORRECTION

PATENT NO. : 11,185,719 B2
APPLICATION NO. : 14/600782
DATED : November 30, 2021
INVENTOR(S) : Michael H. Slayton et al.

It is certified that error appears in the above-identified patent and that said Letters Patent is hereby corrected as shown below:

In the Specification

Column 9, Eq. (2), Line 16, " $\frac{\partial h(r,t)}{\partial t} - \alpha \nabla^2 T(r,t) = \frac{h(r,t)}{\rho C_p}$ " should be -- $\frac{\partial T(r,t)}{\partial t} - \alpha \nabla^2 T(r,t) = \frac{h(r,t)}{\rho C_p}$ --.

Signed and Sealed this
Seventh Day of June, 2022

Katherine Kelly Vidal
Director of the United States Patent and Trademark Office